United States Patent [19]

Schroeder et al.

[11] Patent Number: 5,766,639
[45] Date of Patent: Jun. 16, 1998

[54] COMPOSITION AND METHOD FOR REDUCING MOLECULAR DEFECTS IN NON-RENEWING CELLS

[75] Inventors: John Schroeder, Schenectady; Gillray L. Kandel, Troy, both of N.Y.

[73] Assignee: Rensselaer Polytechnic Institute, Troy, N.Y.

[21] Appl. No.: 645,445

[22] Filed: May 13, 1996

Related U.S. Application Data

[63] Continuation-in-part of Ser. No. 158,024, Nov. 26, 1993, Pat. No. 5,516,534.

[51] Int. Cl.$^6$ ............................ A61K 33/43; A61K 33/14
[52] U.S. Cl. ........................ 424/602; 424/610; 424/663; 424/673
[58] Field of Search ................................ 424/602, 610, 424/663, 673

[56] References Cited

U.S. PATENT DOCUMENTS 4,490,351 12/1984 Clark, Jr. .
5,096,918 3/1992 Mallion .

OTHER PUBLICATIONS

Publication entitled "Overview of the Current Attempts Toward the Medical Treatment of Cataract", Author–Peter F. Kador; Ophthalmology, vol. 90, No. 4, Apr. 1983, pp. 352–364.
N.E. Barklage and J.W. Jefferson, Psychosomatics, The Journal of the Academy of Psychosomatic Medicine 28:No. 5 (1987).
J.J. Corbett et al., Neurology 39:481–487 (1989).
K. DasGupta and J.W. Jefferson, General Hospital Psychiatry 123–97 (1990).
F.T. Franunfelder et al., J Toxicol–Cut & Ocular Toxicol 11(2):97–169 (1992).
J.W. Jefferson, in *Current Psychiatric Therapy*, D.L. Dunner (Ed.), W.B. Saunders Company, Philadephia PA (1993), pp. 246–254.
J.W. Jefferson and J.H. Greist, in *Comprehensive Textbook of Psychiatry* 5th Ed. vol. 2, H.I. Kaplan and B.J. Sadock (Eds.), Williams & Wilkins, Baltimore, Maryland (1989), pp. 1655–1662.
J.W. Jefferson and J.H. Greist, Hospital Therapy 12:74–99 (1987).

F.N. Johnson, in *Depression & Mania: Modern Lithium Therapy*, F.N. Johnson (Ed.), IRL Press, Oxford, Washington, D.C. (1987), pp. 245–246.
T. Kasamatsu et al., Brain Research 558:157–162 (1991).
P.L. Kaufman et al., Acta Ophthalmologica 63:327–332 (1985).
M. Schou, in *Depression & Mania: Modern Lithium Therapy*, F.N. Johnson (Ed.), IRL Press, Oxford, Washington, D.C. (1987), pp. 44–50.
M. Schou, J Psychiatr Res 22:287–296 (1988).
H.C. Stancer and N. Forbath, Arch Intern Med 149:1042–1045 (1989).
U.S. Dept. of Health and Human Services Publication No. (ADM) 91–1868, Bipolar Disorder) (1991).
"Current and Potential uses of Lithium", Academic Highlights of a symposium sponsored by the FMC Corporation, Lithium Division, at the Annual Meeting of the American Psychiatric Association in San Francisco, California (May 7, 1989).
"Lithium & Manic Depression: A Guide", published by the Lithium Information Center and the Dean Foundation for Health, Research and Education, Madison, Wisconsin (1992).
J.J. Harding et al., Acta Ophthalmologica 67:518–524 (1989).
J.J. Harding and R. Van Heyningen, British Journal of Ophthalmology 72:809–814 (1988).
J.M Seddon et al., Arch Ophthalmol 109:252–255 (1991).
B.E.K. Klein et al., Diabetes Care 10:495–499 (1987).
N.E. Isaac et al., Arch Ophthalmol 109:256–260 (1991).
W.K. Clair et al., British Journal of Ophthalmology 73:173–176 (1989).
R. Peto et al., British Medical Journal 296:313–316 (1988).
H. Cheng, British Journal of Ophthalmology 76:257 (1992).
*Handbook of Aqueous Electrolyte Solutions*, by A.L. Horvath, Ellis Horwood Limited, Chichester (1985), pp. 9–33.

Primary Examiner—Zohreh Fay
Attorney, Agent, or Firm—Heslin & Rothenberg, P.C.

[57] ABSTRACT

The invention provides a composition and method for reducing molecular defects in metastable tissue systems. Molecular defects represent spaces or vacancies in the structural order of the metastable system. The effect of molecular defects can be minimized such that the pre-defect order is preserved through the use of structure makers. These structure makers will then occupy the space or vacancy of the molecular defect, preserving the pre-defect order of the system. Lithium ions are a preferred structure maker.

13 Claims, 2 Drawing Sheets

COMPOSITION AND METHOD FOR REDUCING MOLECULAR DEFECTS IN NON-RENEWING CELLS

CROSS REFERENCE TO RELATED APPLICATIONS

This application is a continuation-in-part of earlier application Ser. No. 08/158,024 filed Nov. 26, 1993 now U.S. Pat. No. 5,516,534, the entire disclosure of which is incorporated herein by reference.

FIELD OF THE INVENTION

This invention relates in general to a composition and method for reducing structural changes in proteins and preventing their subsequent effects in metastable biological systems, and more particularly to the use of structure makers (also referred to as structure formers or structure promoters), such as lithium, fluoride ions, calcium ions, hydroxide ions and triethylammonium ions, to reduce and/or prevent disorder in the structure of lens cells, ova, neurons and osteocytes.

BACKGROUND OF THE INVENTION

Age is a significant risk factor in cataract formation, and the cataracts that develop in the elderly are referred to as senile cataracts. In addition, cataracts can arise from trauma or as by-products of disease, or they may be congenital in nature. Cataracts are also thought to result from the use of certain drugs, such as alcohol [see J. J. Harding and R. Van Heyningen, British Journal of Ophthalmology 72:809–814 (1988)], phenothiazine drugs and haloperidol [see N. E. Isaac et al., Arch Ophthalmol 109:256–260 (1991)], and allopurinol [see W. K. Clair et al., British Journal of Ophthalmology 73:173–176 (1989)].

In any type of cataract, opacification (phase separation of the lens protein and subsequent devitrification) is the chief cause of the visual loss. It is therefore desirable to find a method of reducing and/or preventing cataracts. Certain drugs, such as aspirin, aspirin-like analgesics (paracetamol, ibuprofen), and cyclopenthiazide (a diuretic) are thought to have a protective or beneficial effect on the development of cataracts. See J. J. Harding et al., Acta Ophthalmologica 67:518–524 (1989); J .J. Harding and R. Van Heyningen, British Journal of Ophthalmology 72:809–814 (1988); J. M. Seddon et al., Arch Ophthalmol 109:252–255 (1991); B. E. K. Klein et al., Diabetes Care 10:495–499 (1987); and H. Cheng, British Journal of Ophthalmology 76:257 (1992). Although several drugs are currently used or are under investigation for reduction or prevention of cataract formation, a need continues to exist for an efficacious method which can readily be used without adverse side effects on humans.

SUMMARY OF THE INVENTION

This need is met by the composition and method according to the subject invention. A composition is provided for reduction of structural changes in proteins in metastable tissue systems. The composition comprises molecular defect-reducing amounts of a structure maker and a physiologically acceptable carrier.

Further in accordance with the subject invention, a method is provided for reducing molecular defects in a metastable tissue system which comprises selecting a metastable tissue system having molecular defects therein, and exposing the system to a structure maker. The structure maker attenuates the effect of the molecular defects present in the metastable tissue system. Also provided is a method for reducing molecular defects in metastable tissue systems which comprises selecting metastable defect ridden tissue systems, and exposing the system ex situ to a structure maker. Once the structure maker has diminished the effects of the defects in the metastable tissue system, this may then be returned to its in situ site.

In all cases, the structure maker diminishes the effects of the molecular defects and therefore prevents the subsequent formation of further pathology in the metastable tissue system so treated.

As used herein, a metastable tissue system refers to those biological systems in which the cell protein structure is in disorder. The person of skill will be familiar with metastable states in biological systems. Gunton and Droz [Introduction to the Theory of Metastable and Unstable States, Springer-Verlag (1983)], which is incorporated herein by reference, discusses metastability and its persistence over long periods of time and the effect of impurities, vacancies and dislocations on the establishment of equilibrium in metastable systems. Unstable and metastable tissue systems, which are not in equilibrium, include not only the crystalline lens [see Horwitz Investigative Ophthalmology & Visual Science 34, 10–22 (1993),] but also ova [see Guyton Textbook of Medical Physiology, Seventh Edition, 968 (1986)] neurons [see Molecular Biology of The Cell, Third Edition, Alberts et al. 1119 and 1120 (1994)] and osteocytes [Alberts 1182 to 1184]. The method of the invention may be applied to vacancies and disorders in the structure of cells of the lens and any other metastable system in which the same cells are present for long periods of time. Such long-lived cells include for example, ova, neurons, and osteocytes.

Defects can occur in the molecules in these systems, and these defects can be detected by measuring the photoluminescence of the tissue systems. [See J. Schroeder, et al., Mat. Res. Symp. Proc. 272: 251–263 (1992)]. Photoluminescence is an indicator that microscopic defects exist in the ordering of the system, irrespective of whether the system is a solid state system or a biological system. In either type of system, the photoluminescent spectral response of the system provides evidence for the existence of microscopic structural defects within that system.

For example, in the metastable system that comprises the crystalline lens of the eye, an increase in the photoluminescence intensity occurs over time with the intensity of photoluminescence increasing with age. [See also the confirmation of this effect called autofluorescence (sic) in the work of P. J. Airaksinen et al., Invest. Ophthal. Vis. Sci. 34: 762 (1993 Suppl.)]. Molecular defects in the tissue of the lens of the eye are believed to be the precursor modes for formation of cataracts. These structural defects manifest themselves in changes in the photoluminescence response spectrum of the lens.

If plotted as intensity versus wavelength, photoluminescence spectra exhibit a change in intensity, a broadening of spectral band width, and a shift in the wavelength of the peak toward longer wavelength with age. Thus, the presence of molecular defects that eventuate in a clinical cataract can be detected by measuring the photoluminescence response of the lens and determining its deviation from the norm.

In vitro measurements of photoluminescence of a lens and of other thinly-sliced tissue systems can be made using a Raman Spectrometer system comprising an Argon-ion Laser (manufactured by Spectra Physics, Mountain View, Calif.) and a Spex Double Monochromator (manufactured by Spex Industries, Metuchen, N.J.) with subsequent photon counting/detection and stabilization equipment, and a data handling microprocessor also provided by Spex Industries.

Structure makers, structure formers and structure promoters as the terms are used herein refer to ions of very high charge density and very low mass and small ionic radii that can preserve order and in turn can affect the degree of phase separation of the metastable system. A molecular defect can be viewed as a space or vacancy of microscopic dimensions (molecular or atomic in size) within the structure of the protein system. The structure maker occupies that space or vacancy so as to maintain the system in the same order as existed before the molecular defect was produced. The degree of potential order of the system, which relies on the presence or absence of such molecular defects, can be significantly influenced by the number of these molecular defects.

Structure makers are known in the field of aqueous electrolyte solutions to accomplish a similar ordering of the system, and generally include ions smaller and more highly charged than potassium ($K^+$). The term "structure maker" generally refers to a monovalent ion having a mass less than 40 and a Goldschmidt radius less than or equal to 1.33 Å or a divalent ion having a mass less than 41 and a Goldschmidt radius less than or equal to 0.94 Å. Although this general description encompasses most known structure makers, a few known structure makers do fall outside this genus. An important exception is triethylamine or the triethylammonium ion. Preferred structure makers include lithium ($Li^+$), fluoride ($F^-$), calcium ($Ca^{2+}$), triethylammonium ($Et_3NH^+$) and the hydroxyl radical ($OH^-$). Ben-Naim [*Journal of Physical Chemistry*, 79 1268–1274 (1975)], which is incorporated herein by reference, discusses the theory of structure makers and structure breakers in relation to his particular system which is water (see page 1272). The compositions of the subject invention utilize the structure makers to reduce the effect of molecular defects on protein systems. Lithium salts such as lithium chloride and lithium carbonate are preferred in in vivo systems. At suitable doses they are well tolerated by humans who can ingest in excess of 1000 mg/day for extended periods of time without significant untoward risk.

BRIEF DESCRIPTION OF THE FIGURES

The features and advantages of this invention will be evident from the following detailed description of preferred embodiments when read in conjunction with the accompanying drawings in which.

DETAILED DESCRIPTION OF THE INVENTION

Figure 1:
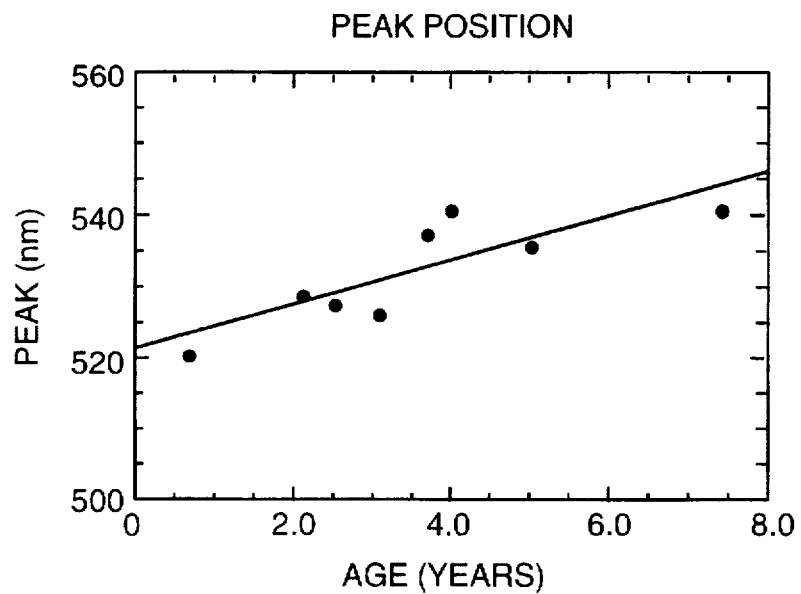
FIG. 1 is a graph showing the red-shift of photoluminescence spectral peak position versus age for eight (8) in vitro human lenses.

This invention teaches that no description of the transmission of electromagnetic waves (light) through biological tissues will be complete without measuring and understanding photoluminescence and absorption, as well as the scattering of the light, in the tissue medium. These three factors, photoluminescence, absorption and scattering, together determine the fate of any electromagnetic wave (ray of light) that passes through any tissue. All three factors change with external perturbations and time (age) in determinable and deterministic ways.

For example, in cataract, photoluminescence, absorption and scattering of electromagnetic waves are elevated relative to age-matched lenses. The elevation can be detected in the retinal plane of the eye by visual tests suitably designed to reflect such elevations. In other biological tissues that are not necessarily completely transparent to visible light but are prepared such that the optical density is sufficiently low (i.e. very thin sections), these same factors can be assessed in in vitro biopsied material with the above-mentioned optical instruments. Again, however, the existence of molecular defects and indicators of metastability provide evidence of the tissue changes correlated with other diseases or altered states. The measured magnitudes of these three factors in all cases are determined by the nano-structural (mesoscopic) details of the tissue, namely, the molecular defects or nano-inhomogeneities that exist in the molecular make-up of the tissue.

In those molecular cell components of biological systems that exhibit properties found in metastable systems, and also in systems exhibiting molecular defects (as determined by their response to optical excitation), the incidence of molecular defect migration and subsequent folding and multiplication can be inhibited by the incorporation of certain classes of ions into these tissues. These classes of ions are generally grouped under the generic term of "structure makers". In general, the structure makers will consist of ions of small ionic radii and well-defined high charge densities, for example lithium ions. Although this analysis is particularly appropriate to the human crystalline lens and the formation of senile cataracts, it is not limited to this system only and applies to any other metastable tissue system. In this context, metastable tissue systems comprise systems in which cytoplasm proteins are non-renewable. Cells found in such systems include ova, neurons, osteocytes and human lens cells.

The mechanisms of the structural changes and the eventual phase separation process leading to senile cataract formation are similar to those that exist in a solid solution. Over time the process is initially on a microscopic scale (i.e., dimensions of several nanometers). However, with further degradation, macroscopic dimensions are achieved (i.e., micron size) with the consequent onset of a pathological state (as exhibited by the changes in the transparency that occur in the cataractous lens which manifests itself in increased scatter, photoluminescence and absorption). However, this same analysis applies to any other biological system that exhibits such molecular defects, or vacancies, in combination with metastability.

Cytoplasmic protein molecules prone to develop structural disorder and metastability appear in those proteins of aging cells that are not renewable during the organism's lifetime. The red blood cells of the human, for example, have a lifetime of a few months, and once they die they are replaced by newly developed red blood cells which take the place of those that have died. The cells of the innermost part of the crystalline lens, on the other hand, are formed in the embryo and persist, in an essentially lifeless form devoid of their ribosomic, mitochondrial and nucleic organelles, throughout the lifetime of the organism. Similarly some cells of the nervous system, also laid down in the embryo, last the lifetime of the organism without renewal. Neurons, however, are not lifeless; they have all those organelles, and carry on the usual functions of living cells except reproduction. The ova of the human female are similarly laid down in the embryo, numbering many thousands at that time. At the birth of the female, however, the number will have dwindled to a few thousand and will have diminished further throughout her reproductive years. Human bone cells represent an intermediate form of cell renewal wherein approximately ten percent of the existing osteocytes are renewed each year.

The consequence of this cell longevity is to expose the long lived cells to the hazards of physiologic insult, with no possibility to correct the changes wrought by age in the cytoplasm of these cells. They thus bear the accumulated scars of the organism's history and render the tissue they comprise subject to those pathologies that are correlated with aging. Thus, for example, Alzheimer's dementia, senile cataract, and osteoporosis all tend to make their appearance in later life, with the incidence of each rising after the age of sixty.

Down's syndrome is another age correlated disorder. It occurs not in the aging mother, but rather as the result of the fertilization of her aged ova. The incidence of births of children with Down's syndrome is more than thirty times higher in mothers age forty five or older than it is in women who are less than thirty years old. Premature forms of Alzheimer's dementia and lenticular opacification (i.e., cataract) both appear in persons born with Down's syndrome and attest to the power of the protein aging process that affects structures in a succeeding generation.

Those skilled in the biomedical arts know that structural disorder due to aging, and to other insults to the lens protein, results in phase separation and opacification of the lens cytoplasm. This process leads to a physiological epiphenomenon in that tissue system, but, if it were not for the fact that the resulting opacification interferes with vision, the changes in the cytoplasm would go unnoticed. Owing to the fact that the lenticular cells are lifeless and barely carry on any significant interactive functions with other cells of the body, it is only because of the change in lens transparency that the altered protein structure is noticed. Neurons, on the other hand, carry on most of the functions of other body cells, except for reproduction; hence the altered protein structure associated with age in these cells may interfere with both intracellular and intercellular relationships. This interference results in manifest pathology unrelated to the tissue's transparency. However, the optical changes of the aged cytoplasm of neurons are the same as those occurring in the lenticular cytoplasm owing to the devitrification process. The resulting changes in photoluminescence, increased scatter and absorption are detectable ex situ by optical measurement covering the entire spectral range, including the x-ray regime.

Experiments in vitro have shown, for example, that human lenses immersed in a physiological saline (NaCl) solution, 20% of which is LiCl, a structure maker, exhibit changes that may be detected by precise optical measurements. These changes can be interpreted as a reversal of the normal aging process of the lens. The data for treatment with a non-structure maker (KCl) when comprising 20% of a physiological saline show no comparable effect. These results are given in Table 1. Eyes from the same donor were employed in the comparison of the structure maker to non-structure maker, i.e., one eye of the donor was exposed to the structure maker, LiCl, while the opposite eye was exposed to the non-structure maker, KCl.

Referring to FIG. 1, the substantially linear increase of the position of the photoluminescent peak of lenses by age is shown. The linear progression establishes that as the lens ages, a shift to longer wavelengths (i.e. red-shift) in peak position occurs; this is indicative of an increase in molecular defects within the lens system.

Figure 2:
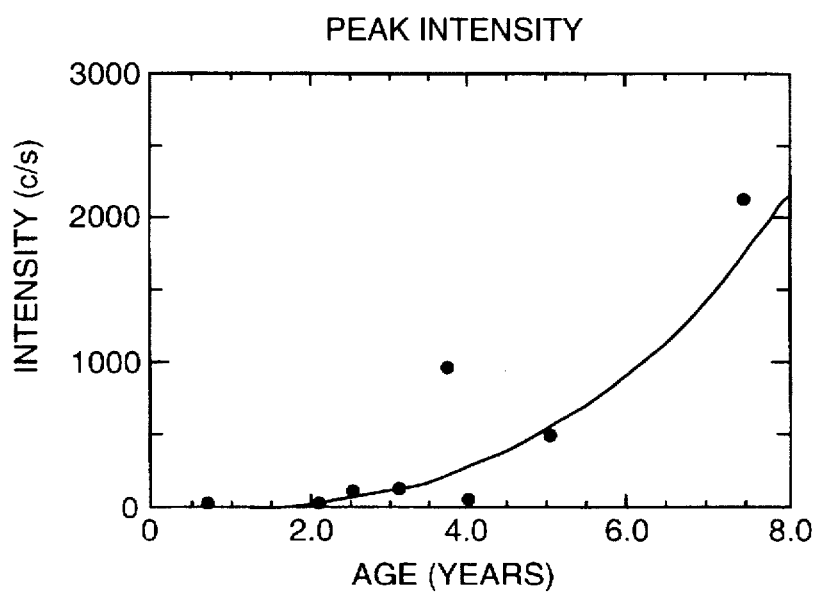
FIG. 2 is a graph showing photoluminescence peak intensity versus age for the same set of human lenses as shown in FIG. 1.

Referring to FIG. 2, the intensity of the peak photoluminescence is plotted as a function of age, again showing an increase over time. If log of intensity were plotted, a linear progression would be seen, establishing that as the lens gets older, an increase in peak intensity occurs; this is also indicative of an increase in molecular defects within the lens system.

Figure 3:
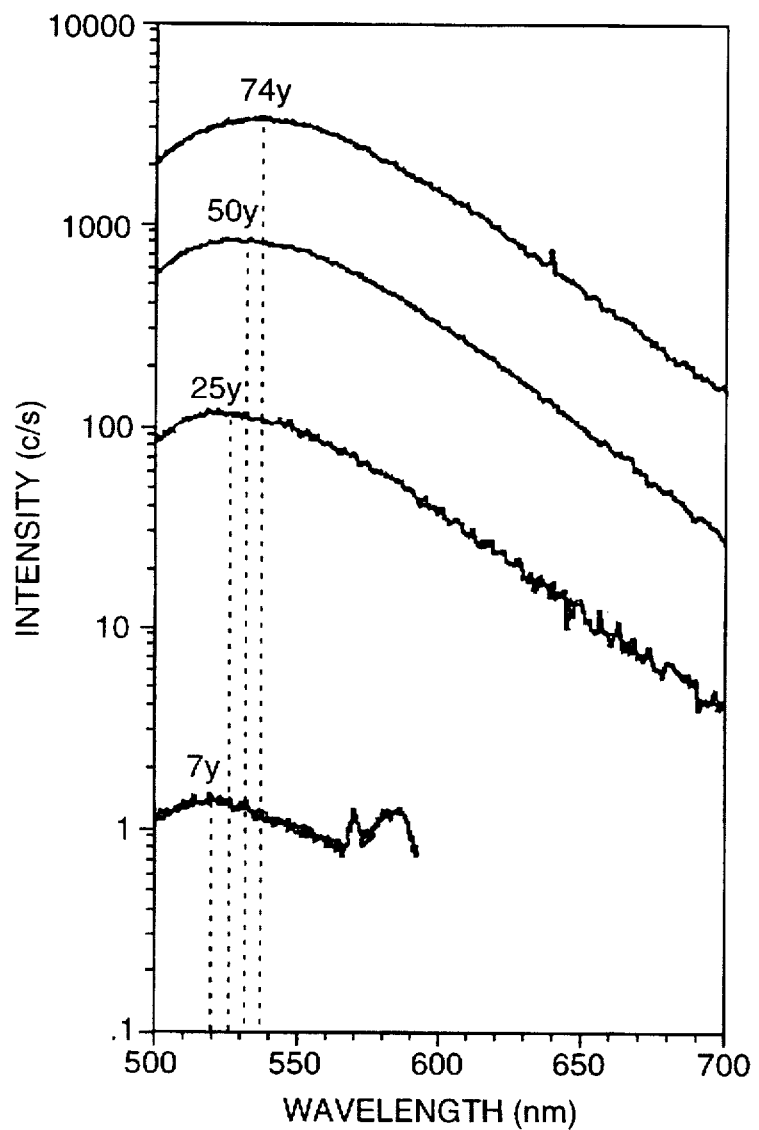
FIG. 3 is a graph showing photoluminescence intensity versus wavelength for four (4) in vitro human lenses.

FIG. 3 shows the photoluminescence intensity plotted against wavelength for four human donor lenses of various ages (74 years, 50 years, 25 years, and 7 years). The exciting wavelength is 488 nm. Note that as the number of molecular defects increase in the lenses due to the increasing age of the donor, there is an increase in the peak intensity, a broadening of the spectral band (i.e., the full width of the peak at half maximum photoluminescence intensity), and a shift in the wavelength of the peak. These three changes are characteristic of the presence of increasing numbers of molecular defects within these systems. This analysis is supported by similar spectral behavior in a glass, a disordered solid system, where the three spectral properties of photoluminescence, absorption and scattering change similarly as structural defects increase and the solid becomes more devitrified. [See J. Schroeder, Light Scattering of Glass. Treatise on Materials Science and Technology, Vol. 12, Glass I: Interaction with Electromagnetic Radiation (1977), pp. 157–222, Academic Press Inc., New York; and J. Schroeder et al., Mat. Res. Soc. Symp. Proc. 272: 251–263 (1992)].

The effect of the structure makers on these characteristic age changes of the human lens was determined by immersing one each of a matched pair of lenses for at least one hour at room temperature in a physiological saline solution (NaCl), 20% of which consisted of isomolar lithium chloride (LiCl) or isomolar potassium chloride (KCl). The results of these tests are shown in Table 1. With lithium ion treatment, the shift of the peak position to a longer wavelength is reversed, i.e. the mean peak wavelength before treatment was 532.4 nm, and the mean position after treatment with a structure maker was 527.9 nm. This decrease in the mean peak position (−4.5 nm shift) is indicative of a reduction in the number of molecular defects as discussed above and is equivalent in both donors to the number of molecular defects that would accumulate in a fourteen year period.

When a non-structure maker bath is used, the mean shift is only −0.6 nm. Thus it is clear that structure makers such as lithium salts are able to alter the effect of the molecular defects in the lens and produce a blue-shift in the peak of the photoluminescence spectrum. These observations of in vitro human donor lenses treated with lithium ions are consistent with the protection afforded against selenium induced cataracts in Wistar suckling rats. [X. R. Huang, et al., Invest. Ophthal. Vis. Sci. 34: 1064 (1993 Suppl.)]. Note moreover that selenium ions are classified as structure breakers and consequently produce molecular defects leading to cataractogenesis.

As discussed above, the in vitro donor lenses were exposed to lithium ions by immersion in a solution containing lithium salts. The lithium ions could also be administered in vivo, in the case of the eye, in the form of eye drops which would permit a smaller total dose to be more localized to the crystalline lens. Moreover, diffusion of the lithium ions to the lens or other tissue could be facilitated by iontophoresis, the small diameter of the lithium ions lending itself admirably to this route of entry. If confined to this route of entry, 30 mg of LiCl/day in an isomolar physiological saline carrier provides an efficacious dose. However, where a systemic route must be employed, daily doses up to 750 mg may be required.

In summary, the data show that ions identified as structure makers, such as lithium, are an effective treatment for lenticular molecular defect management and an effective means to alter opacifying molecular defects in lenses in which there is an increased photoluminescence, absorption and scatter resulting from disorder in the nanostructural matrix. In addition, the aforementioned methods are also applicable to other non-renewable cells and to osteocytes.

TABLE 1

Blueshift in the Peak Photoluminescence Values With Treatment

|  | 20% Li$^+$ | 20% K$^+$ |
|---|---|---|
| before treatment* | $v_{1,1} = 526.7$ nm<br>$v_{1,2} = 538.0$ nm | $v_{1,1} = 526.2$ nm<br>$v_{1,2} = 537.0$ nm |
| after treatment* | $v_{1,1} = 522.4$ nm<br>$v_{1,2} = 533.3$ nm | $v_{1,1} = 525.2$ nm<br>$v_{1,2} = 536.8$ nm |
| variation due to treatment | $\Delta_1 = -4.3$ nm<br>$\Delta_2 = -4.7$ nm | $\Delta_1 = -1.0$ nm<br>$\Delta_2 = -0.2$ nm |

*treatment consists of immersion for at least one hour at room temperature in isotonic saline solution (NaCl) 20% of which consists of isomolar lithium chloride, or potassium chloride Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined by the following claims.

What is claimed is:

1. A method of reducing molecular defects in a metastable tissue system other than a human lens which comprises:

selecting a metastable tissue system, other than a human lens, comprising cells having molecular defects therein; and exposing said cells in said metastable tissue system to a structure maker, said structure maker comprising an ion chosen from the group consisting of Li$^+$, Ca$^{2+}$, F$^-$ and OH$^-$ thereby reducing said molecular defects in said metastable tissue system and delaying phase separation.

2. The method of claim 1 wherein said cells are neurons.

3. The method of claim 1 wherein said cells are ova.

4. The method of claim 1 wherein said cells are osteocytes.

5. The method of claim 1 wherein said structure maker comprises lithium ions.

6. The method of claim 5 wherein said lithium ions are furnished by lithium chloride.

7. The method of claim 5 wherein said lithium ions are furnished by lithium carbonate.

8. A method of reducing molecular defects in a metastable tissue system other than a human lens which comprises:

selecting a metastable tissue system, other than a human lens, comprising cells having molecular defects therein; and exposing said cells in said metastable tissue system to triethylammonium ion or triethylamine, thereby reducing said molecular defects in said metastable tissue system and delaying phase separation.

9. The method of claim 8 wherein said cells are neurons.

10. The method of claim 8 wherein said cells are ova.

11. The method of claim 8 wherein said cells are osteocytes.

12. The method of claim 8 wherein said cells are non-human lenticular cells.

13. The method of claim 1 wherein said cells are non-human lenticular cells.

* * * * *